United States Patent
Downs (10) Patent No.: US 10,709,600 B2
(45) Date of Patent: Jul. 14, 2020

(54) STRETCH MARK REMOVAL DEVICE

(71) Applicant: Ronald Downs, Mishawaka, IN (US)

(72) Inventor: Ronald Downs, Mishawaka, IN (US)

(73) Assignee: THE CENTRE, P.C., Mishawaka, IN (US)

( * ) Notice: Subject to any disclaimer, the term of this patent is extended or adjusted under 35 U.S.C. 154(b) by 11 days.

(21) Appl. No.: 13/623,773

(22) Filed: Sep. 20, 2012

(65) Prior Publication Data

US 2013/0073010 A1  Mar. 21, 2013

Related U.S. Application Data

(60) Provisional application No. 61/536,790, filed on Sep. 20, 2011.

(51) Int. Cl.
*A61F 7/00* (2006.01)
*A61N 5/06* (2006.01)

(52) U.S. Cl.
CPC .............. *A61F 7/00* (2013.01); *A61N 5/0616* (2013.01); *A61F 2007/0001* (2013.01); *A61F 2007/0077* (2013.01); *A61F 2007/0088* (2013.01); *A61N 2005/0644* (2013.01); *A61N 2005/0659* (2013.01); *A61N 2005/0661* (2013.01)

(58) Field of Classification Search
CPC ........ A61B 18/203; A61B 2018/00452; A61B 2018/00476
USPC ............................................................ 606/9
See application file for complete search history.

(56) References Cited

U.S. PATENT DOCUMENTS

| | | | |
|---|---|---|---|
| 6,214,034 B1 | 4/2001 | Azar | |
| 6,551,347 B1* | 4/2003 | Elkins | A61F 7/0085 165/46 |
| 6,702,837 B2* | 3/2004 | Gutwein | A61N 5/0616 606/9 |
| 6,991,644 B2* | 1/2006 | Spooner et al. | 607/88 |
| 7,309,335 B2 | 12/2007 | Altshuler et al. | |
| 7,431,719 B2 | 10/2008 | Altshuler et al. | |
| 2002/0156509 A1* | 10/2002 | Cheung | A61F 7/007 607/96 |
| 2003/0004499 A1* | 1/2003 | McDaniel | A61B 18/203 606/3 |
| 2003/0204227 A1* | 10/2003 | Ingram | A61F 7/02 607/114 |
| 2004/0147984 A1 | 7/2004 | Altshuler et al. | |
| 2007/0049998 A1 | 3/2007 | Conrad et al. | |
| 2007/0198004 A1* | 8/2007 | Altshuler et al. | 606/9 |

(Continued)

FOREIGN PATENT DOCUMENTS

WO    2003047682 A2    6/2003

OTHER PUBLICATIONS

Lightwave LED to zap stretch marks away, Plasmetic, Aug. 22, 2007. available at http://www.plasmetic.com/skin/stretch-marks/lightwave-led-to-zap-stretch-marks-away.html.*

(Continued)

*Primary Examiner* — John R Downey
(74) *Attorney, Agent, or Firm* — Neal, Gerber & Eisenberg LLP (57) ABSTRACT

A stretch mark removal device having a first portion that includes a plurality of light emitting devices each positioned on a surface of the first portion, a heating unit extending along the surface of the first portion between the light emitting elements and a handle coupled to the first portion.

9 Claims, 4 Drawing Sheets

(56) References Cited

U.S. PATENT DOCUMENTS

| | | | |
|---|---|---|---|
| 2008/0077202 A1* | 3/2008 | Levinson | A61F 7/02 607/96 |
| 2008/0188915 A1* | 8/2008 | Mills | A61F 7/007 607/112 |
| 2010/0145321 A1* | 6/2010 | Altshuler et al. | 606/9 |

OTHER PUBLICATIONS

YouTube video entitled "get rid stretch marks Phoenix | Scottsdale Arizona" uploaded by user "SuddenlySlimmer" on Dec. 18, 2009. available at https://www.youtube.com/watch?v=Z3OnwRflfmk.*
International Search Report and Written Opinion for PCT/US2013/060693 Filed Sep. 19, 2013; 9 pages.

* cited by examiner

STRETCH MARK REMOVAL DEVICE

RELATED APPLICATIONS

This application is a non-provisional patent application that claims the benefit of and the priority from U.S. Provisional Patent Application No. 61/536,790, filed Sep. 20, 2011, titled STRETCH MARK REMOVAL DEVICE.

BACKGROUND OF THE INVENTION

The present invention relates generally to a medical device which reduces the appearance of scars and stretch marks using infrared heating and ultraviolet light.

Stretch marks are a common skin condition and are essentially linear dermal scars accompanied by epidermal atrophy. They are caused by stretching the skin. This skin distension leads to excessive mast cell degranulation with subsequent damage of collagen and elastin. They can affect almost 90% of pregnant women, 70% of adolescents, and 40% of males. The most common sites to be affected by stretch marks include the breasts, buttocks, thighs and lateral abdomen. The appendages normally present in skin—including hair follicles, sweat glands and other structures are absent in areas affected by stretch marks.

As previously mentioned, stretch marks are a form of scarring that takes place in the skin as a result of dermal tearing secondary to stretching. Degranulation of dermal mast cells imparts damage to the elastin and collagen fibrils in the dermis causing them to fracture. This results in thinning of the dermal layer. This loss of structural integrity causes the overlying epidermis to atrophy. Stretching of the skin is not the sole cause. Genetic factors altering collagen ratios in the skin and glucocorticoids produced in the body or taken medically can also contribute. Stretch marks are less likely to form with adequate dermal sub-structure. They are more likely in people with a high body mass index (BMI), low maternal age, weight gain if greater than about 15 kg., or people with a higher than normal neonatal birth weight.

Stretch marks appear initially as reddish or purplish lines in the skin with palpable contour irregularities. Just like other scars, they acutely initiate the inflammatory reaction needed to heal with subsequent vascular dilatation in the wound area giving the reddened or purplish color. Localized swelling may initially give the stretch mark a raised contour which subsides as the edema fades. Although permanent, they mature over time as the vascular dilatation resolves and scar remodeling takes place leaving a less noticeable but permanent defect.

Since damaged collagen fibrils are at the center of the problem, it is beneficial to understand collagen in order to help repair it. Collagen is a subunit of larger aggregates called fibrils. It is typically about 300 nm in length and 1.5 nm in width. It is comprised of 3 polypeptide chains called alpha chains. They are "left handed" helices twisted together to form a "right Handed" coil called a triple helix. These helices are stabilized by hydrogen bonding. They contain a regular arrangement of amino acids. The fibrils are semi crystalline aggregates of collagen molecules bundled together called fibers. These fibers are arranged in different combinations and concentrations in various tissues to provide the various tissue qualities. Skin is made up of mostly type I and type III collagen, Type III being mostly reticular fibers.

Treatment is aimed at repairing the damaged collagen fibrils and diminishing aesthetic impact with early treatment being optimal. Various treatments are available for the purpose of improving the appearance of existing stretch marks, including laser treatments, dermabrasion, and prescription retinoids. In addition, the use of a pulsed dye laser has been shown to increase pigmentation in darker skinned individuals with repeated treatments. However, if the epidermis and the dermis has been penetrated, laser will not remove the stretch marks.

A surgical procedure for removing lower abdominal stretch marks is the tummy tuck, which removes the skin below the navel where stretch marks frequently occur. A new modality, fractional laser resurfacing, offers a novel approach to treating striae. Using scattered pulses of light only a fraction of the scar is zapped by the laser over the course of several treatments. This creates microscopic wounds. The body responds to each treatment by producing new collagen and epithelium.

While each of these procedures provide varying levels of success in the removal, or reduced appearance, of stretch marks, all of these procedures are performed using very expensive equipment in a physician's office. Accordingly, a need exists for a portable, simple to use device which will allow for the removal of stretch marks from the skin.

BRIEF SUMMARY OF THE INVENTION

Other systems, methods, features, and advantages of the present invention will be or will become apparent to one with skill in the art upon examination of the following figures and detailed description. It is intended that all such additional systems, methods, features, and advantages be included within this description, be within the scope of the invention, and be protected by the accompanying claims.

One embodiment of a skin mark removal device has an upper portion, which includes a first surface with a plurality of light emitting devices mounted thereon. The light emitting elements are configured to emit a light of a predefined frequency. A heating element is surrounds the light emitting devices and is configured to generate a predefined amount of heat. A lower end of the upper portion is affixed to a handle. The handle extends away from the upper portion and is contoured to ergonomically fit into the human hand.

In one embodiment, the first surface is covered with a light reflecting material which is used to direct light from the light emitting devices away from the first surface.

In another embodiment, the device includes a shroud that covers the sides of the device to prevent the disbursement of light and heat.

In another embodiment, the device includes a control unit that modulates the amount of light and heat produced by the device.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

Figure 1:
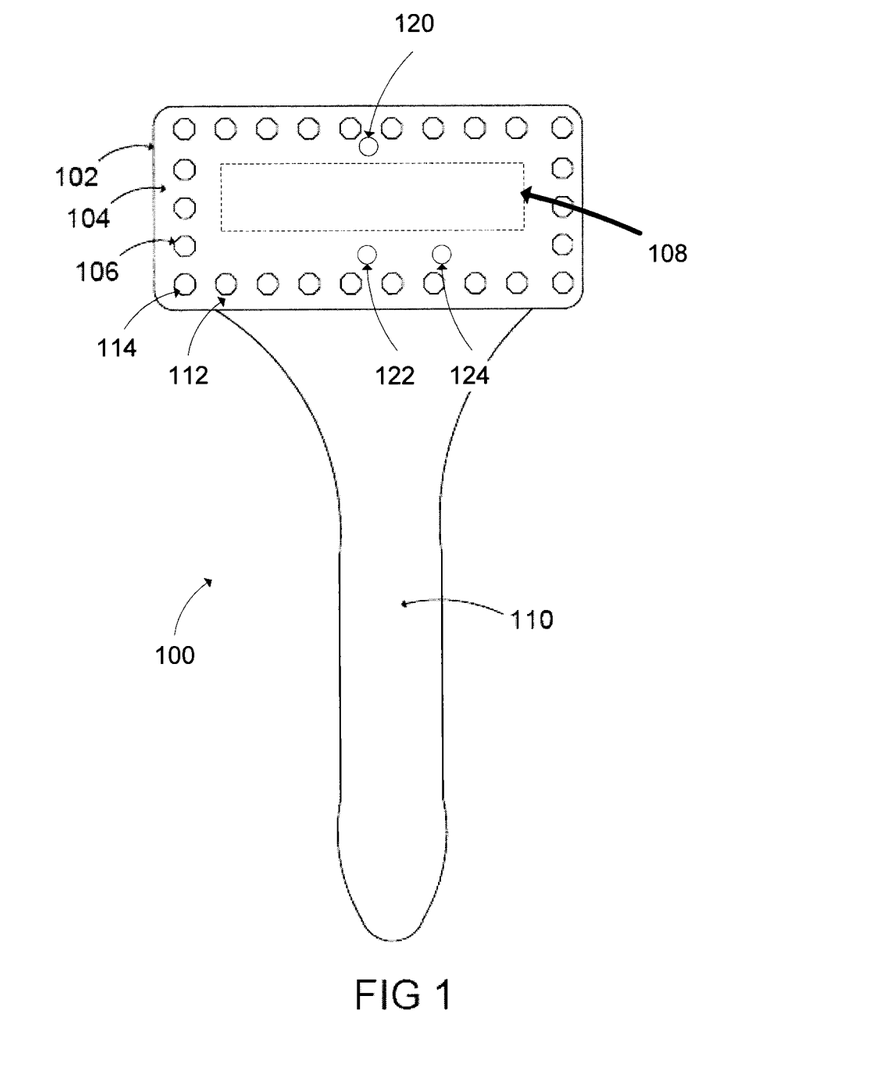
FIG. 1 depicts one embodiment of the skin mark removal device that is consistent with the present invention.

FIG. 1 depicts one embodiment of a stretch mark removal device 100 that is consistent with the present invention. The device 100 includes an upper portion 102 which includes a first surface 104 having a plurality of light emitting elements 106 mounted thereon. The light emitting elements 106 are configured to emit a light of a predefined frequency. A heating element 108 is positioned between the light emitting elements 106 and is configured to generate a predefined amount of heat. The heating element 108 may extend around each of the light emitting devices 106 such that the heating element 108 surrounds each light emitting element 106. A lower end of the upper portion is affixed to a handle 110. The handle 110 extends away from the upper portion 102 and is contoured to ergonomically fit into the human hand. The handle 110 may also extend from an upper end of the upper portion to a lower end of the upper portion in an arc shape. The handle may be made from any rigid material including, but not limited to, plastic. The first surface 104 may be covered with a light reflecting material which is used to direct light from the light emitting devices 104 away from the first surface 104.

The light emitting elements 106 may be arranged around the periphery of the first surface 104 of the upper portion 102 or may be equally spaced across the first surface 104 of the upper portion 102. The light emitting elements 106 may be light emitting diodes ("LED"). Each of the light emitting elements 106 are electrically coupled to a power supply (not shown). The power supply may include a conventional power cord configured to electrically couple to a 120 or 208 VAC power outlet, a battery or any other power source capable of providing power to a light emitting device 106. Each of the light emitting elements 106 are configured to generate a predefined wavelength of light. The predefined wavelength may be between approximately 620 nm and approximately 650 nm, preferably 633 nm.

The upper portion 102 may be rotatably affixed to the handle 110 such that the upper portion 102 can rotate towards and away from the skin. The upper portion 102 may also be rotatably affixed to the handle 110 such that the upper portion can rotate 360 degrees in relation to a central axis of the handle 110.

A thermally conducting plate 112 may be mounted over the heating unit 108. The thermally conductive plate 112 may be configured to uniformly distribute the heat generated by the heating unit 108. The thermally conducting plate 112 may be manufactured from a thermal conducting metal including, but not limited to, copper, steel, stainless steel or any other metal or metal alloy capable of conducting heat. A first surface of the thermally conducting plate 112 may be in contact with the skin of the user while a second surface of the thermally conducting plate 112 is in contact with the heating element 108. The heating element may also be incorporated into the thermally conducting plate 112. The thermally conducting plate 112 may also be separated from the surface of the skin by a predefined distance.

The thermally conducting plate 112 includes a plurality of openings 114 that correspond to the light emitting elements 106 when the thermally conducting plate 112 is positioned on the upper portion 102 of the device 100. The openings 114 are sized to each accommodate at least one light emitting element 106. The thermally conducting plate 112 may also be configured such that an upper portion of each light emitting element 106 is substantially flush with a top surface of the thermally conducting plate 112. A thermally conductive fluid may be applied to the skin of the user to enhance the operation of the heating element 108. The thermally conducting fluid assists in the uniform transfer of heat from the heating unit 108 to the surface of the skin.

Figure 2:
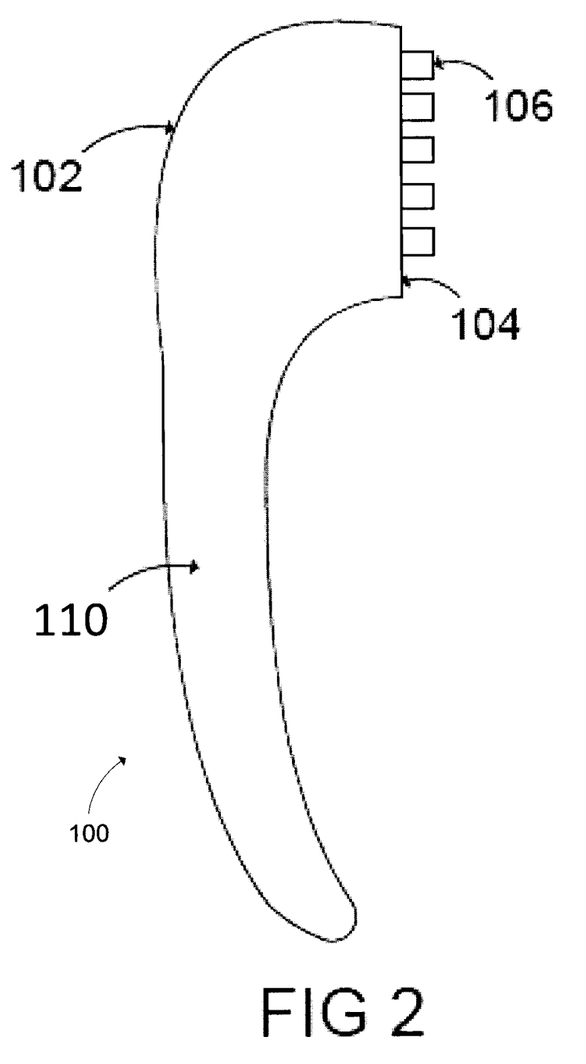
FIG. 2 depicts one embodiment of a side view of the device with the light emitting devices extending beyond the upper portion of the device.

FIG. 2 depicts a side view of the device 100 with the light emitting elements 106 extending beyond the upper portion 102 of the device 100. Consistent with this embodiment, the first surface 104 is flush with the end of the upper portion 102 of the device 100 such that the light emitting elements 106 extend beyond the plane of the upper portion 102 of the device 100.

Figure 3:
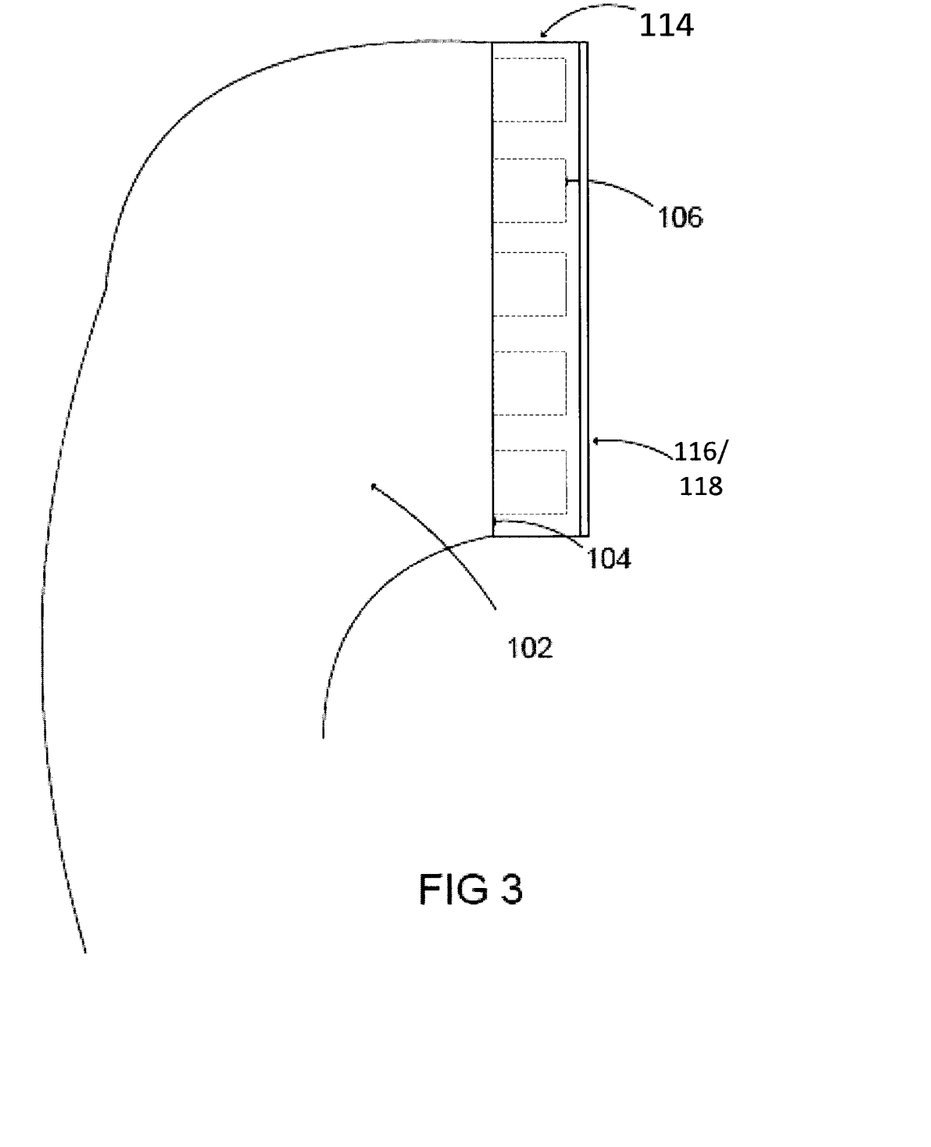
FIG. 3 depicts another embodiment of a side view of the device with the light emitting elements including a light shroud covering the light emitting devices.

FIG. 3 is a side view of another embodiment of a side view of the device 100 including a flexible light shroud 114 covering the sides of the first surface 104. Consistent with this embodiment, the light emitting elements 106 are positioned on the front surface 104 of the upper portion 102 and the flexible shroud 114 is affixed to the periphery of the front surface 104 such that the light emitting elements 106 are surrounded by the shroud 114. The shroud 114 may be manufactured of a flexible material including, but not limited to, rubber or latex. The shroud 114 may be made from a material that does not emit light to prevent light generated from the light emitting elements 106 from escaping the shroud 114. The inner surface of the shroud 114 may be covered in a light reflective material which reflects light from the light emitting elements 106 away from the inner surface of the shroud 114. The shroud 114 may extend outward from the front surface 104 to a distance sufficient to engage a portion of the human body such that a light and substantially heat proof seal is created between the shroud 114 and the portion of the human body in contact with the shroud 114. The shroud 114 may also extend past the surface of the light emitting devices 106.

A lens 116 may be positioned in the shroud 114 over the front of the upper portion 102. The lens 116 may be configured to focus the light from the light emitting elements 106. Consistent with this embodiment, the lens 116 is inserted into the open end of the shroud 114, and is held in position by a channel on the inner surface of the shroud 114. The lens 116 may be manufactured of a flexible material which is capable of conforming to the contours of the human body such as clear plastic. The lens may be attached to the shroud 114 by clips, adhesive, a ridge on the inner periphery of the shroud 114, or by any other securing method. In addition, the lens 116 may be capable of conducting heat in a uniform fashion across the surface of the lens 116. The lens 116 may be removably affixed to the front of the upper portion 102.

A filter 118 may be placed over the front of the upper portion 102. The filter 118 may be configured to allow only a certain wavelength of light to exit the device 100. The filter 118 may also be incorporated into the lens 116. The filter may be configured to allow light at a wavelength of between approximately 620 nm to approximately 650 nm to pass through.

Figure 4:
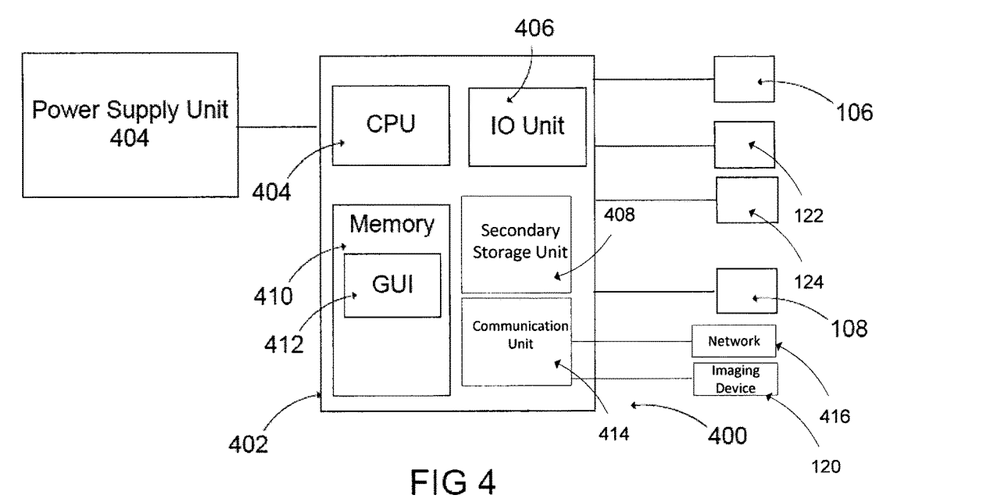
FIG. 4 depicts one embodiment of a control panel used to control the light emitting device.

FIG. 4 depicts one embodiment of a control panel 400 used to control the light emitting device 100 that is encompassed the handle. The control panel 400 may also be an external device connected to the device 100 via a cord or cable. The control panel 400 includes a central control unit 402 which is electrically coupled to each of the light emitting elements 106 and the heating unit 108. The central control unit 402 includes a central processing unit (CPU) 404, an input output (I/O) unit 406 such as an analog to digital converter, a secondary storage device 408, and a memory 410. The I/O unit 406 may further include a plurality of analog outputs which provide a variable voltage or current to the heating element 108 and the light emitting elements 106. The I/O unit 406 also includes a plurality of inputs which are electrically coupled to sensors which monitor environmental conditions related to the operation of the device.

The central control unit 402 may include a Graphical User Interface ("GUI") 412 in the memory 410 which is used to display information via a display device connected to the I/O unit 402 as described herein. The GUI 412 includes any user interface capable of being displayed on a display device including, but not limited to a display panel in an executable program or any other interface capable of being displayed on a computer screen. Further, the GUI 412 may also be stored in the secondary storage unit 408.

The central control unit 402 is electrically coupled to a power supply 404. The power supply 404 can be any type of power supply unit capable of providing adequate power to the light emitting elements 106 and the heating unit 108. The power supply unit 404 may be an electrical plug which is connected to a 120 or 208 VAC power outlet or a battery coupled to the control unit.

The control unit 402 may be electrically coupled to each of the light emitting elements 106 individually via the I/O unit 406. In another embodiment, the control unit 402 is electrically coupled to groups of light emitting elements 106 via the I/O unit 406. The control unit 402 is configured to vary the power supplied to each of the light emitting elements 106 such that the total wavelength of all of the light emitting elements 106 is between approximately 620 nm and approximately 650 nm, preferably 633 nm, at a predetermined intensity. In one embodiment, the control unit 402 is electrically coupled to a light level sensor 122 which transmits the total light level emitted from the light emitting elements 106 to the control unit 402 via the I/O unit 406. The light level sensor 122 may be positioned on surface of the thermal plate 112 such that the light level senor 122 reads in the light generated by light emitting elements 106 surrounding the light level sensor 122. Additional light level sensors 122 may be positioned on the surface of the thermal plate 112 and coupled the control unit 402 via the I/O unit 406. Consistent with this embodiment, software operating in the CPU 404 of the control unit 402 modulates the power to each light emitting device 106 individually, or in groups, to maintain a constant light level output form the device 100 using programmable control loops that are known in the art.

The control unit 402 also provides power to the heating unit 108 via an analog output on the I/O unit 406 of the control unit 402. Software operating in the CPU 404 of the control unit 108 modulates the heating unit 108 such that the heating unit 108 does not exceed a predefined temperature setpoint. In one embodiment, the control unit 404 monitors the amount of heat generated by the heating unit 108 to maintain the predefined setpoint. In another embodiment, the control unit 402 monitors the surface temperature of the skin and modulates the heat output from the heating unit 108 to maintain a constant skin surface temperature, or heating element temperature. Consistent with this embodiment a surface temperature sensor is used to measure the temperature of the skin. The surface temperature sensor 124 may include, but is not limited to, an infrared sensor, a thermistor, a thermocouple or any other temperature sensor capable of measuring the surface temperature of human skin. The temperature sensor 124 is mounted on the surface of the thermal plate 112 such that the temperature sensor 124 reads the temperature of the thermal plate, or the temperature of the skin surface. Additional temperature sensors may also be mounted on the thermal conducting plate 112 and coupled to the control unit 402 via the I/O unit 406. In one embodiment, the predefined skin surface temperature is approximately 105 degrees Fahrenheit to 110 degrees Fahrenheit, preferably approximately 106.8 degrees Fahrenheit.

In another embodiment, the control unit 402 includes an imaging device 120, such as a camera, coupled to I/O unit 406 which captures images of the area covered by the shroud 114. The imaging device 120 may be digital camera positioned in an opening in the thermal plate 112. The imaging device 120 may be any known digital imaging device 120 including a CCD digital camera, a SLR digital camera, or any other known imaging device 120. The imaging device 120 includes a memory, a processor, and an image sensor, such as a CCD or CMOS sensor. The imaging device 120 may be coupled to the control unit 402 via a data connection such as, but not limited to a fire wire connection, a USB connection, or any other data connection. To capture an image, the control unit 402 illuminates the region under the shroud 114 using the light emitting elements 106 before capturing an image of the area covered by the shroud 114. Once the image is captured, it is stored along with user information and a date/time in the storage unit 408 using a conventional image format including, but not limited to, the JPEG image format.

The control unit 402 may also include a communication unit 414 configured to transmit the captured images to at least one computing device connected to the communication unit 414 via a network 416. The network 416 is of a type that is suitable for connecting the computing devices for communication, such as a circuit-switched network or a packet-switched network. The network 416 may include a number of different networks, such as a local area network, a wide area network such as the Internet, telephone networks including telephone networks with dedicated communication links, connection-less network, and wireless networks. Consistent with this embodiment, the transmitted images can be used by the user or a physician to track the progress of treatment.

The control unit 402 may also store the skin temperature readings, light level readings, operating temperatures of the heater and images of the stretch mark over time in a treatment storage unit in the secondary storage 408. Consistent with this embodiment, the control unit 402 transmits the data to a second computer or display device via I/O ports electronically coupled to the control unit 402. The control unit 402 may include an external port (not shown) that allows the data in the secondary storage unit 408 to be transferred to an external storage device.

The control unit 402 may allow a user to adjust settings of the device 100 via the GUI 412. Consistent with this embodiment, the user can adjust attributes such as, but not limited to, the light level intensity, the operating time of each treatment session, the intensity of the heater, the operational time of the heater, the operational time of the lighting, or any other attribute of the device 100 via a display unit (not shown) coupled to the control unit 402.

Because the device 100 is portable, patients can effectively utilize the device 100 at home without having to travel to a physician for costly and expensive conventional treatments. Further, thermal energy applied to the skin at a safe level, between approximately 105 degrees Fahrenheit to 110 degrees Fahrenheit, preferably 106.8 degrees Fahrenheit, not only relaxes the fibrils but also simulates the collagen molecule to form new molecules and repair itself.

The thermal energy also promotes local thermal-regulated vasodilatation facilitating the healing process by improving the nutrient and building block delivery to the healing microenvironment. Light at between approximately 620 nm and 650 nm, preferably 633 nm, penetrates the dermis up to a 1.5 mm depth into the dermis and up regulates Procollagen I and III, the building blocks of the collagen molecule. Collagen forms into bundles as it regenerates and lessens the appearance of the stretch mark. When used together these two energy sources become synergistic. The thermal energy not only stimulates collagen production on its own but improves local microcirculation and relaxes the fibril exposing more of the collagen molecule to the LED energy.

Figure 5:
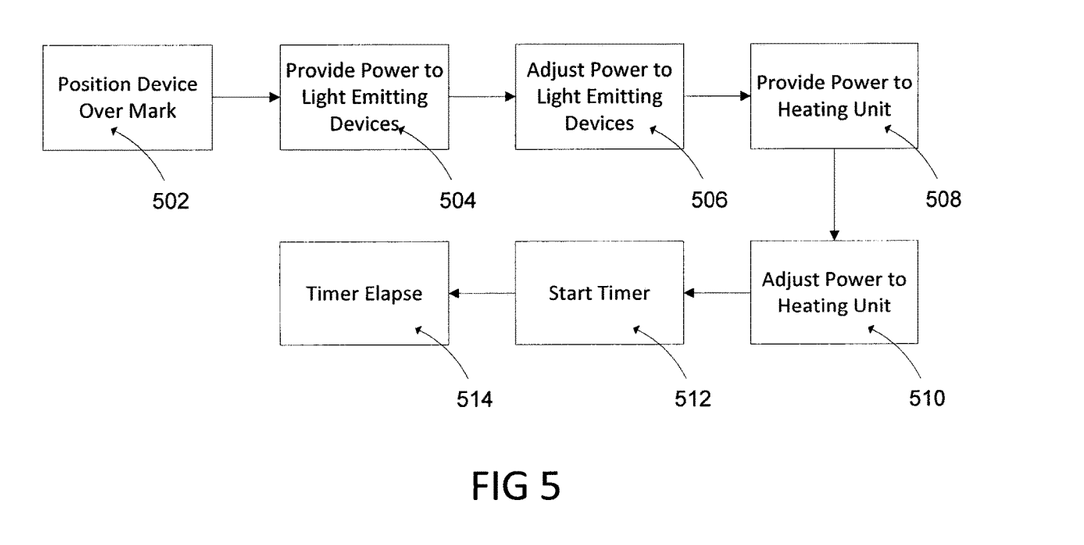
FIG. 5 depicts a schematic representation of the operation of the device of FIG. 1.

FIG. 5 depicts a method of treating a stretch mark using the stretch mark removal device 100. In step 502, the device is positioned over a portion of skin having a stretch mark such that the light emitting devices 106 and heating element 108 are opposite the surface of the skin. In other words, the light emitting devices 106 and heating element 108 face the surface of the skin. In step 504, the control unit 402 triggers an output to provide power to the plurality of light emitting elements 106. In step 506, the control unit 402 adjusts the power provided to each light emitting elements 106 until a signal from a light level sensor 122 indicates that the light emitting elements 106 are producing light at a predetermined intensity.

In step 508, the control unit 402 triggers an output providing power to the heating element 108. In step 510, the control unit 40 adjusts the current provided to the heating unit 108 in response to a temperature signal from a temperature sensor. Alternatively, the control unit 402 may simultaneously provide power to the light emitting elements 106 and the heating element 108. In step 512, the control unit 402 initiates a timer that maintains the temperature and intensity setpoints for a predetermined period of time. In step 514, the control unit 402 turns off the heating unit 108 and the light emitting elements 106 when the timer elapses.

All patents referred to herein, are hereby incorporated by reference, whether or not specifically done so within the text of this disclosure. In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A stretch mark removal device comprising:
a first portion including a plurality of light emitting devices positioned on a surface of the first portion;
a heating unit extending along the surface of the first portion between the plurality of light emitting elements such that the heating element surrounds each of the plurality of light emitting devices;
a thermally conducting plate configured to conduct heat from the heating unit,
a thermally conducting fluid between the thermally conductive plate and a skin surface of a user; and
a handle rotatively coupled to the first portion such that the first portion rotates towards the handle and around a central axis of the handle;
a control unit electrically coupled to the heating unit and each light emitting device that is configured to provide control signals to each light emitting device to adjust the power supplied to the light emitting devices to control the wavelength of the light generated from each light emitting device based on a signal sent to the control unit from a light sensor positioned adjacent to at least one light emitting device such that the light emitting elements generate light at a total wavelength of 633 nm, and to provide control signals to the heating unit to adjust the amount of heat generated by the heating unit based on a signal sent to the control unit from a temperature sensor on the surface of the thermally conducting plate,
wherein
the thermally conducting fluid evenly distributes heat across the skin surface of the users and
a front surface of the thermally conductive plate is parallel with the front surface of the plurality of light emitting devices.

2. The stretch mark removal device of claim 1 wherein the heating unit heats a surface to between 105 degrees Fahrenheit to 110 degrees Fahrenheit.

3. The stretch mark removal device of claim 1, wherein the thermally conductive plate is coated with a light reflecting film.

4. The stretch mark removal device of claim 1, including a shroud affixed to the periphery of the first portion, wherein the shroud is made of a material that does not transmit light.

5. A method of treating stretch marks comprising:
positioning a first surface of a device having a plurality of light emitting elements and a heating unit surrounding each of the plurality of light emitting devices over a portion of a human body;
applying a thermally conducting fluid between a thermally conductive plate and the portion of the human body;
generating light at a predetermined wavelength while simultaneously heating the surface to a predetermined temperature by the heating unit;
maintaining the illumination of the light emitting elements and the heating of the surface for a predetermined period of time;
adjusting the power supplied to each light emitting device to control the wavelength of the light generated from each light emitting device based on a signal sent to the control unit from a light sensor positioned adjacent to at least one light emitting device such that the light emitting diodes generate light at a total wavelength of 633 nm, and providing control signals to the heating unit to adjust the amount of heat generated by the heating unit based on a signal sent to the control unit from a temperature sensor on the surface of the thermally conducting plate, and turning off the heating unit and light emitting elements by the control unit after the predetermined time has elapsed, wherein the thermally conducting plate is positioned on the heating unit and is configured to conduct heat from the heating unit, the thermally conducting fluid evenly distributes heat across the portion of the human body, and a front surface of the thermally conductive plate is parallel with the front surface of the plurality of light emitting devices.

6. The method of claim 5, wherein the heating element heats the surface to between 105 degrees Fahrenheit to 110 degrees Fahrenheit.

7. The method of claim 5, wherein the thermally conductive plate is coated with a light reflecting film.

8. The method of claim 5 wherein a shroud is positioned on the periphery of the first portion.

9. The method of claim 8 wherein the shroud is made of a material that does not transmit light.

* * * * *